US00PP34436P3

(12) United States Plant Patent
Khayat

(10) Patent No.: US PP34,436 P3
(45) Date of Patent: Jul. 26, 2022

(54) BANANA PLANT NAMED 'RSV'

(50) Latin Name: *Valery*
Varietal Denomination: 'RSV'

(71) Applicant: Eliyahu Khayat, Nahariya (IL)

(72) Inventor: Eliyahu Khayat, Nahariya (IL)

(73) Assignee: RAHAN MERISTEM (1998) LTD, Rosh Hanikrah (IL)

( * ) Notice: Subject to any disclaimer, the term of this patent is extended or adjusted under 35 U.S.C. 154(b) by 0 days.

(21) Appl. No.: 17/132,055

(22) Filed: Dec. 23, 2020

(65) Prior Publication Data

US 2022/0201910 P1 Jun. 23, 2022

(51) Int. Cl.
*A01H 5/08* (2018.01)
*A01H 6/00* (2018.01)

(52) U.S. Cl.
USPC ..... Plt./160

(58) Field of Classification Search
USPC ..... Plt./160
CPC ..... A01H 6/00; A01H 5/08
See application file for complete search history.

*Primary Examiner* — Keith O. Robinson
(74) *Attorney, Agent, or Firm* — Lyn Marantz; KK Patents, LLC

(57) ABSTRACT

'RSV' is a mutant of 'Valery' selected on the merits of being a shorter cultivar while simultaneously being a more productive cultivar for the grower. 'RSV' shows the following characteristics:

More productive due to an additional 2 marketable hands per bunch,
Longer fingers,
And a higher number of fingers in a bunch.

The most important characteristic of 'RSV' is its lower stature that will contribute to more efficient agronomic practices such as;

Fruit harvesting, bunch bagging, and better wind tolerance.

15 Drawing Sheets

'RSV' is a new cultivar derived from mutating 'Valery' which is a known (Khayat 2021) 'Cavendish' sub-variety commonly grown in tropical countries, especially in Northern Colombia, Santa Marta, and Uraba, where the climate fluctuates between long rainy periods interrupted by dry periods that can stretch over a period of a few weeks with almost no rainfall. Some of the soils in these regions have high levels of salinity. Banana growers in these regions prefer 'Valery' due to its ability to mitigate the lack of water during the dry periods. On the other hand, the high humidity in the rainy intervals is conducive to infections of Black Leaf Streak Disease (BLSD) caused by *Mycosphaerela fijiensis*. 'Valery' shows higher tolerance to BLSD compared to other 'Cavendish' sub-varieties. The drawback of 'Cavendish' is the height of the plant, reaching approximately 4.5 m in $R_1$ (second harvest) and 5 m in $R_2$ (third harvest). In $R_3$ the height reaches 5.5 m. In the past we have created a very short variety named 'ADI' (U.S. Plant Pat. No. 20,645), using invitro mutagenesis. The aim here was to use the same tools to reduce the stature of 'Valery'. Given the importance of 'Valery' in Santa Marta Colombia, we have used initials (explants) from Santa Marta and screened the mutants in the same region.

An extensive process of tissue culture was used by augmenting the number of subcultures and the inclusion of Thidiazuron (TDZ) and high levels of Benzyl aminopurine (BA) in the growth media. The in-vitro process included:

i. 20 explants were selected in a Santa Marta plantation and were introduced to an invitro culture. The meristems were extracted and placed on a medium containing MS base medium and 2.5 mg $L^{-1}$ BA, 3% sucrose and 0.8% agar solidifier. The meristems were incubated for 5 weeks at 22° Celsius under florescent lighting at a regime of 16/8 dark/light hours. The meristems were subdivided longitudinally into 3 sub-meristems that were each cultured separately. Each of the 20 sub-meristems was incubated for an additional 4 weeks as per the above-described environmental conditions.

ii. In each subculture the BA was doubled reaching 10 mg $L^{-1}$ BA from subculture 0 to 2. From subculture 3 to 12 in addition to the BA, 2 mg. $L^{-1}$ TDZ was added to the medium.

iii. After 12 subcultures in 10 mg $L^{-1}$ BA and 2 mg $L^{-1}$ TDZ the clumps were separated and meristems were transferred to a medium devoid of cytokinins that included 2 mg $L^{-1}$ IBA for shoot elongation and root development.

iv. Each clump contained 2-4 plantlets that were each put in a test tube with the rooting medium as described above. All plants derived from a single clump were defined as "siblings" that were annotated with the same accession number.

v. Finally, we had in total approximately 15,000 plants belonging to approximately 7000 accessions. Following hardening the plants were planted in the field in the Santa Marta region at a density of 1750 plants per hectare. The accessions were separated in the field.

vi. The height and fruit bunch parameters were measured for each accession in cycles 1-2 ($R_0$ and $R_1$). A record was taken on plant stature, the number of marketable fruit per bunch, fruit size, bunch weight, total number of hands in the bunch, and length of bunch. Due to complexity of the determining the male and female hands on a bunch, we can only estimate that there are approximately 13 female hands on a bunch.

vii. The best 8 accessions were recycled in the tissue culture lab. Each clone (defined as plants from the same accession number) was multiplied to 150 plants.

viii. The clones were planted in a new location in the same region in a completely random arrangement at 1750 plants per Hectare.

ix. Data was collected clonally, as described above, two clones were selected and named 'RSV' and '1192A'.

x. Based on yield and height, 'RSV' was preferred.

BACKGROUND OF THE INVENTION

Most domesticated banana genotypes are triploid and parthenocarpic. Despite a wealth of germplasm with a wide range of qualitative and quantitative traits, remote markets prefer the 'Cavendish' (*Musa acuminata* Cola AAA). Being widely demanded by consumers in the export markets the 'Cavendish' is irreplaceable. But due to sterility and the triploid nature of 'Cavendish', breeders have a very narrow set of tools to improve this variety. The natural mode of propagation of 'Cavendish' is through suckers that formed from rhizomes. In recent years the majority of growers use plants that are produced by tissue culture laboratories. Interestingly, despite the common origin, 'Cavendish' plants segregate to distinct cultivars that display a variety of polymorphic traits, especially in the context of plant architecture, yield and fruit characteristics (Khayat 2021). For example, the cultivar 'ADI 9107' is at least 1.5 meters shorter than its originator cultivar 'Zelig', while 'Valery' is approximately 2 m taller than 'Zelig'. Despite these great differences in height, they both belong in the 'Cavendish' group of cultivars and share several traits such as sensitivity to diseases and pests, and lack of tolerance to extreme environmental conditions. Their common taste and shape make the cultivars indistinguishable in the market place. However, growers in different regions have a clear favorite cultivar.

Plant height is an important agro-technical parameter in banana plantations. Tall cultivars are more difficult to handle. Almost all growers bag the fruit bunch to avoid sun-burns and protect the fruit from bacteria, fungi, insects and birds. Growers in tropical areas are forced to remove older leaves infected with black sigatoka disease. Furthermore, fruit harvesting is difficult in tall trees. In addition, tall cultivars are susceptible to windy conditions and consequentially require physical support. All of these practices are more difficult to execute for higher stature plants.

'Valery' (*Musa acuminata* Cola AAA variety 'Cavendish' subvariety 'Valery') is the tallest 'Cavendish' subvariety grown commercially for export, reaching up to 5.5 m from the ground level to the curved portion of the peduncle. Other subvarieties are significantly shorter (approximately 3.5 m for 'Grand Naine' and 2.3 m for 'ADI'). Nevertheless, despite the difficulties of growing super tall plants, certain growers prefer 'Valery' over shorter subvarieties. 'Valery' is the main subvariety used in the two main banana growing regions of, Uraba and Santa Marta, Colombia. The main reasons are high yield and excellent bunch structure with long fingers. In addition, 'Valery' is a robust subvariety, tolerant to water deficiency and black streak leaf disease, a severe fungal disease in bananas.

The present invention relates to the development of a short 'Valery' cultivar named 'RSV' with an improved bunch weight without compromising the positive traits of the subvariety.

To this end, we have used an extensive tissue culture with high levels of proliferating hormones. These in-vitro conditions are known to induce somaclonal variation. This method was proven effective in activation of retro-transposable elements that induce stable mutations in plants (Khayat 2021).

The primary selection of the initials 'Valery' plants was performed in Santa Marta Colombia. Twenty explants were extracted from corms. The meristems were placed in tissue culture in Meristemos Colombia laboratory (Rio Negro, Colombia). The initials were sent to Rosh Hanikra, Israel where they were asexually multiplied by tissue culture as delineated below. The process entailed 22 subcultures in a Murashigi and Skoog medium containing 10 mg $L^{-1}$ Benzyl aminopurine (BA) and 3% sucrose. In the growth medium of subcultures 3 to 12, 2 mg $L^{-1}$ of Thidiazuron (TDZ) was added in order to induce mutagenesis. The combination of TDZ and a relatively high BA concentration over 12 subcultures was proven to induce mutations (Khayat 2021). Subsequently, the ex-vitro plants were sent back to Colombia after hardening for selection and validation. The process of selection was first performed on siblings of each clone, 3-5 plants per clone. Siblings are defined as plants that originate from the same cluster at cycle 22. After the first selection, 8 best performing clones were multiplied to 150 plants per clone in Meristemos Colombia. These were planted randomly in the field in the Santa Marta region and subsequently compared on a clonal basis. A single clone, 'RSV' out-performed the rest and is the subject of this plant patent.

BRIEF DESCRIPTION OF THE FIGURES

FIG. 1 shows photos of banana plants and fruit bunches of three genotypes: Photo A and Photo D show control 'Valery'; Photo B and Photo E show 'RSV' and Photo C and Photo F show '119A2'. Photo A, Photo B, and Photo C represent the plants from each genotype at the flowering stage, 24 weeks post planting, while Photo D, Photo E and Photo F represent the fruit bunch at harvesting, 35 weeks post planting. The plants were grown using a protocol common in commercial plantations, in Finca Remenso II in the Santa Marta district of Colombia.

FIG. 2 shows the weight of the different genotypes in the first cycle of fruits ($R_0$). The data represent an average of at least 3 plants from each of the genotypes, 'RSV', Control and '119A2'. The plants were grown using a protocol common in commercial plantations, in Finca Llanos in the Santa Marta district of Colombia.

FIG. 3 shows the average number of individual fruit ("fingers") in the second cluster of fruit ("hands") from the top (the top hand is the first hand developed in the fruit bunch), in the first cycle of fruits ($R_0$). The data represent an average of at least 3 plants from each of the genotypes, 'RSV', Control and '119A2'. The plants were grown using a protocol common in commercial plantations, in Finca Llanos in the Santa Marta district of Colombia.

FIG. 4 shows the average plant height at flowering from the ground level to the tip of the curved pedicel in the first cycle of fruits ($R_0$). The data represent an average of at least 3 plants from each of the genotypes, 'RSV', Control and '119A2'. The plants were grown using a protocol common in commercial plantations, in Finca Llanos in the Santa Marta district of Colombia.

FIG. 5 shows the average net bunch weight of the different genotypes in the first cycle of fruits (R0). The data represent an average of 150 plants from each of the genotypes, 'RSV', Control and '119A2'. The plants were grown using a protocol common in commercial plantations, in Finca Llanos in the Santa Marta district of Colombia.

FIG. 6 shows the total number of marketable fingers (in hands 1-8) of the different genotypes in the first cycle of fruits ($R_0$). The data represent an average of 150 plants from each of the genotypes (clonal comparison), 'RSV', Control and '119A2'. The plants were grown using a protocol common in commercial plantations, in Finca Llanos in the Santa Marta district of Colombia.

FIG. 7 shows the average plant height at flowering from the ground level to the tip of the curved pedicel in the first cycle of fruits (R0). The data represent an average of 150 plants from each of the genotypes, (clonal comparison) 'RSV', Control and '119A2'. The plants were grown using a protocol common in commercial plantations, in Finca Llanos in the Santa Marta district of Colombia.

FIG. 8 shows the average number of individual fruit ("fingers") in the second cluster of fruit ("hands") from the top (the top hand is the first hand developed in the fruit bunch), in the first cycle of fruits ($R_0$). The data represent an average of at least 3 plants from each of the genotypes, 'RSV', Control and '119A2'. The plants were grown using a protocol common in commercial plantations, in Finca Llanos in the Santa Marta district of Colombia.

FIG. 9 shows the average net bunch weight of the different genotypes in the second cycle of fruits ($R_1$). The data represent an average of 150 plants from each of the genotypes, 'RSV', Control and '119A2'. The plants were grown using a protocol common in commercial plantations, in Finca Llanos in the Santa Marta district of Colombia.

FIG. 10 shows the total number of marketable fingers (in hands 1-8) of the different genotypes in the second cycle of fruits ($R_1$). The data represent an average of 150 plants from each of the genotypes (clonal comparison), 'RSV', Control and '119A2'. The plants were grown using a protocol common in commercial plantations, in Finca Llanos in the Santa Marta district of Colombia.

FIG. 11 shows the average plant height at flowering from the ground level to the tip of the curved pedicel in the second cycle of fruits ($R_1$). The data represent an average of 150 plants from each of the genotypes, (clonal comparison) 'RSV', Control and '119A2'. The plants were grown using a protocol common in commercial plantations, in Finca Llanos in the Santa Marta district of Colombia.

FIG. 12 shows the average number of marketable hands of the different genotypes in the second cycle of fruits ($R_1$). The data represent an average of 150 plants from each of the genotypes (clonal comparison), 'RSV', Control and '119A2'. Marketable hands are hands in which the minimal finger size exceeds 17 cm. The plants were grown using a protocol common in commercial plantations, in Finca Llanos in the Santa Marta district of Colombia.

FIG. 13 shows the average pseudostem circumference 1 m above ground of the different genotypes in the second cycle of fruits (R1) at flowering. The data represent an average of 150 plants from each of the genotypes (clonal comparison), 'RSV', Control, and '119A2'. The plants were grown using a protocol common in commercial plantations, in Finca Llanos in the Santa Marta district of Colombia.

FIG. 14 is a photo of 'RSV' inflorescence in Finca Llamos in the Santa Marta district of Colombia. The photo is of ($R_1$) fruit cycle occurring 41 weeks post tissue culture and 24 weeks post planting.

FIG. 15. shows a representative fruit size on the second hand from the top of the bunch, 35 weeks post planting.

CHARACTERISTICS OF THE NEW VARIETY

The new cultivar 'RSV' was created from 'Valery' a well-known cultivar used mainly in Columbia. The main drawback of the original 'Valery' is its height. On the other hand, 'Valery' is a robust cultivar which exhibits tolerance to various environmental stresses. The yield in the original 'Valery' is similar or better than other 'Cavendish' cultivars, especially under environmental stress conditions. Our purpose was to create a new cultivar with traits that are similar or better to the original 'Valery' but with a reduced height. 'RSV' is a mutant created through soma clonal variation. The main distinguishing feature of 'RSV' is its reduced height compared to its originator cultivar. FIG. 4, FIG. 7, and FIG. 11 show a difference in height of over 1 meter between 'RSV' and the control plants. This feature is especially apparent in the $R_0$ (FIG. 4 and FIG. 7). The difference in height is expressed in parallel to higher components of yield including higher net weight, higher number of fingers in the second hand and in total per bunch, as well as longer fingers (FIG. 15). The average bunch weight of 'RSV' was 21.5 kg in $R_0$ and 22.8 kg in $R_1$, while the control plants were 18.7 kg and 16 kg respectively for $R_0$ and $R_1$. The large difference in weight in $R_1$ stems mainly from the additional 2 marketable lower hands in 'RSV' compared to the control (FIG. 12).

An additional characteristic of 'RSV' is the length of the fingers in the bottom 1 to 2 hands. While these hands are unacceptable to meet the commerce standards of the original 'Valery', in 'RSV' the fingers in the bottom 2 hands pass the minimal length of 17 cm and as such are marketable.

There is also a difference in the number of fingers per hand between the control and 'RSV'. In the control at $R_1$ we find 22 fingers in the second hand, while in 'RSV' there were 23.5 fingers on the average.

Another important characteristic of the 'RSV' is the circumference of the plant. FIG. 13 shows 64 cm of circumference in 'RSV' at 1 meter above ground level while the control was only 59.6 cm. In general, the thicker pseudostem is more wind resistant.

BRIEF SUMMARY OF THE INVENTION

In the present invention we describe a sub 'Valery' cultivar that features a lower stature, higher bunch weight, higher number of marketable hands on the bunch, longer fingers, and a higher number of fingers in the second hand. Combined these features are the components of yield in banana plants. Thus, the new cultivar exhibits an improved clone compared to the original mother plant. In addition, 'RSV' also has a thicker pseudostem which will make it more resistant to wind, one of the major constraints of 'Valery'. When compared to the most commonly known 'Cavendish' subvariety, 'Grand Naine', normal 'Valery' banana plants are approximately 1.3 to 1.5 meters taller. (Khayat 2021)

DETAILED BOTANICAL DESCRIPTION OF RSV

Detailed botanical description of the new and distinct mutant 'RSV' which includes its general appearance, pseudostem and suckers, petiole, midrib, leaf, inflorescence and male bud, flower bract, male flower, and fruit. This description is based on observations of specimens 41 weeks post tissue culture, grown in a commercial plantation in the Santa Marta region of Colombia. Data were collected between weeks 27 and 32 of 2015. The description is based on an observation of approximately 20 plants grown in a commercial plantation. The height was measured in the first ($R_0$) and the second cycle of fruit ($R_1$) development. The difference in plant height between $R_0$ and $R_1$ is due to the shading of the canopy which is denser in $R_1$. The descriptors presented herein are in accordance with and include all of the 117 international standards found in "Descriptors for Banana (*Musa* spp.)" elaborated by CIRAD/INIBAP/IPGRI. The color terminology is in accordance with The U.K.'s Royal Horticultural Society's Colour Chart, 2001. Ploidy: Triploid (AAA). Leaf habit: upright.

Pseudostem: Height: 196 cm, and 360 cm respectively for $R_0$ and $R_1$ measured from the ground to the highest part of the plant at the point where the peduncle curves downward. The circumference of the pseudostem is 84 cm±6 cm at the time of flower emergence. The leaves generated faster in 'RSV' compared to both the control and '119A2'. Pseudostem color: Light Green (144-A). Appearance: Dull (waxy). Predominant underlying color of the pseudostem: Light Green (145-A). Pigmentation of the underlying pseudostem: no pigments other than chlorophyll. Sap color: clear. Wax on leaf sheaths: Slightly waxy. Number of suckers: 3. Position of suckers: Close to parent (vertical growth). The growth habit of the leaves on the pseudostem is upright.

Petiole: Lenticels at petiole base: Approximately 1.4 cm wide. Lenticel color: Brown (200-B). Petiole canal leaf III: open with margins spreading. Petiole margins: Winged and clasping the pseudostem. Wing type: necrotic. Petiole wing color: Green (146-D). Petiole margin color: Green (142-C). Edge of petiole margin: Very light green-translucent. Petiole margin width: 7 mm.

Leaf blade: Length: 212 cm. Leaf blade width: 65-80 cm. Petiole length: 48-67 cm. Color of leaf upper surface: Green (137-A). Appearance of leaf upper surface: Shiny. Color of leaf lower surface: Green (140-B). Appearance of leaf lower surface: Dull. Wax on leaves: Slightly waxy. Insertion point of leaf blades on petiole: Symmetrical. Shape of leaf blade base: Tapered in first leaves going to both oval in later leaves. Leaf corrugation: Few stripes. Color of midrib dorsal surface: Green (138-B). Color of midrib ventral surface: Green (144-B). Color of cigar leaf dorsal surface: Green (141-A). Lenticels on leaves of water suckers: No lenticels. Venation pattern: parallel venation in the leaf lamina in the pinnate style. Leaf Shape: Oblong with pointy to rounded ends.

Inflorescence/male bud: Peduncle length: 88-92 cm. Peduncle weight 3 Kg. Empty nodes on peduncle: Four or more. Peduncle width: 7.5-9 cm. Peduncle color: Yellow-green (144-A). Peduncle hairiness: Hairless (FIG. 14).

Rachis: Present. Position: Falling vertically. Male bud shape: Ovoid. Male bud size: 32-39 cm. Average diameter of male bud: 15.5 cm.

Bract: Bract base size: Average 16 cm. for the part connected to the rachis. Bract apex shape: Obtuse. Bract length: Average 33 cm. at longest point. Bract width: Average 21 cm. at the widest point. Color of the bract external face: Red-purple (59-A). Color of the bract internal face: Grayed-orange (176-A). Color stripes on bract: lines on the external face: color not measurable on The R.H.S. Chart. Bract scars on rachis: Not prominent. Male bract shape: Ovate. Wax on the bract: Moderately waxy. Presence of grooves on the bract: Moderate. Persistence of the bracts of the rachis is weak.

Male flower: Data taken at completion of flower emergence (see FIG. 14). Male flower behavior: Falling before the bract. Compound tepal basic color: Red-purple (65-A), later becoming grey (192). Lobe color of compound tepal: Yellow (8-A). Free tepal appearance: Corrugated. Style shape: Straight. Stigma color: Orange (25-C). Ovary basic color: Yellow (8-D). Ovary pigmentation: Very few signs of pigmentation.

Fruit position: Slightly curved in the upper hands and curved upward in the lower hands (see FIG. 1). Apex: somewhat rounded. Number of fruit per hand: 23.5 average. Fruit length: 26.5 cm. (when counting the inner hand second from the top, see FIG. 15). Fruit shape longitudinal curvature: Slightly curved. Fruit circumference: 14 cm average. Fruit pedicel length: 4.2 cm. average. Pedicel surface: Hairless. Immature fruit peel color: Green (144-A). Mature fruit peel color: Yellow (14-C). Fruit peel thickness: 2.0 mm. Adherence of the fruit peel: Fruit peels easily. Cracks in fruit peel: Without cracks. Pulp fruit: With pulp. Pulp color before maturity: White (155-D). Pulp color at maturity: (155-D). Fruit is eaten: Ripe. Flesh texture: Firm. Predominant taste: Sweet. Main use: Dessert banana. Presence of seed: No seeds. Longitudinal ridges of fruit: weak. Attitude of the fruit of the bunch: horizontal.

Agronomic characteristics: Averages taken during 2015 for first cycle in a plot of 1750 plants per hectare: Number of true leaves at flowering: 21. Average net (8 marketable hands A grade) 21.49 kg.

TABLE 1

Descriptive Morphological Characteristics:

| | 'RSV' | |
|---|---|---|
| Cultivar | Average | ± Std Err. |
| Number of above ground suckers | 3 | 0.0 |
| Pseudostem circumference, 1 m above ground (in cm) | 84 | 6 |
| Spots are present or absent on the pseudostem | Coffee color | |
| Petiole length CM | 48 | 7 |
| Peduncle length CM | 199 | 56 |
| Peduncle diameter CM | 23 | 5.1 |
| Bunch width CM | 89.5 | 13.3 |
| Bunch length cm (marketable hands) | 136.5 | 6.8 |
| Total Hands in a bunch | 13 | 3 |
| Number of fruit per hand | 17.89 | 1.5 |

It is claimed:

1. 'RSV', a new and distinct mutant plant of the 'Valery' banana cultivar, substantially as illustrated and described, which is between 1-2 meters lower in height than its originator, higher in bunch weight in the first and second cycle of fruit, having 2 additional marketable hands, having more fingers per hand, having longer fingers in the second hand from the top, and having a larger circumference of the pseudostem 1 meter above ground level.

* * * * *

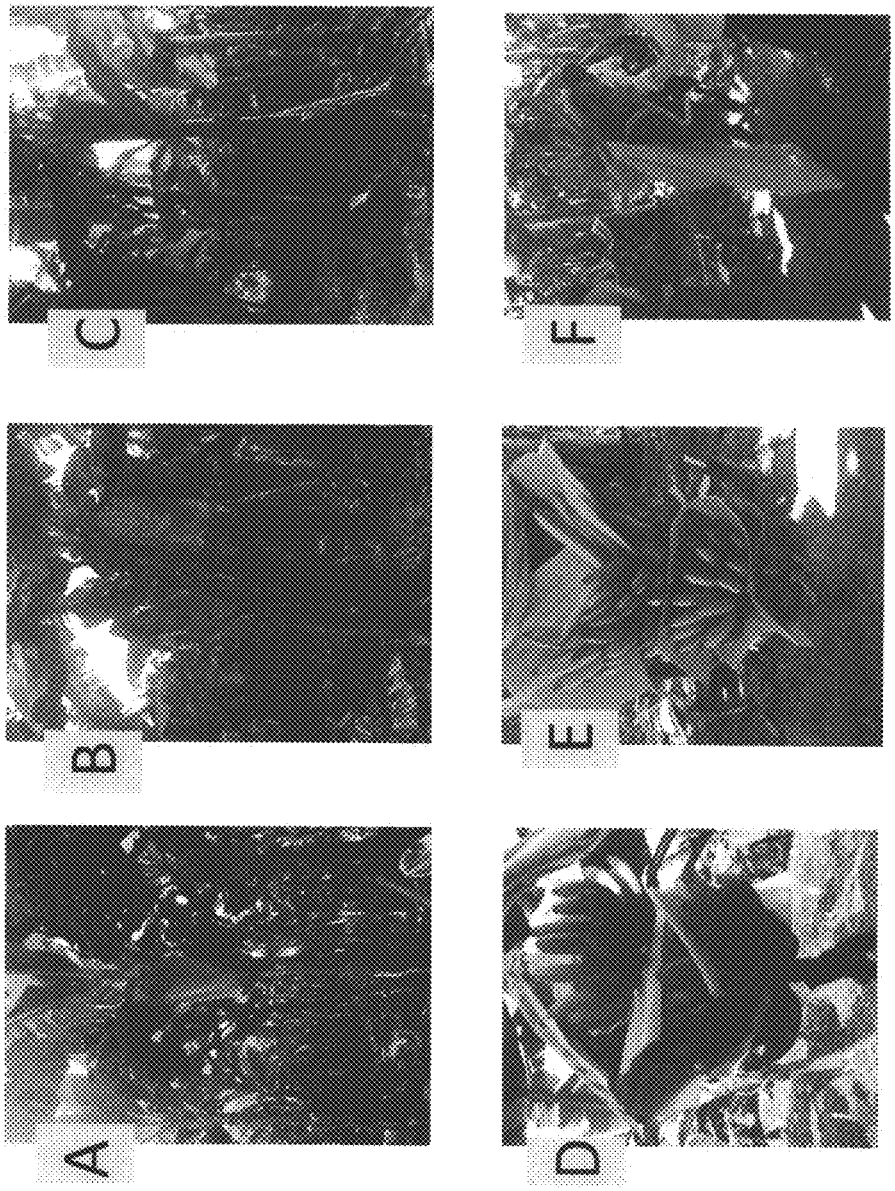
Figures 1A-F:
A – Control Plant at flowering – 24 weeks post planting
B - RSV Plant at flowering – 24 weeks post planting
C – 119A2 Plant at flowering – 24 weeks post planting
D – Control bunch – 35 weeks post planting
E - ERSV bunch – 35 weeks post planting
F – 119A2 bunch – 35 weeks post planting

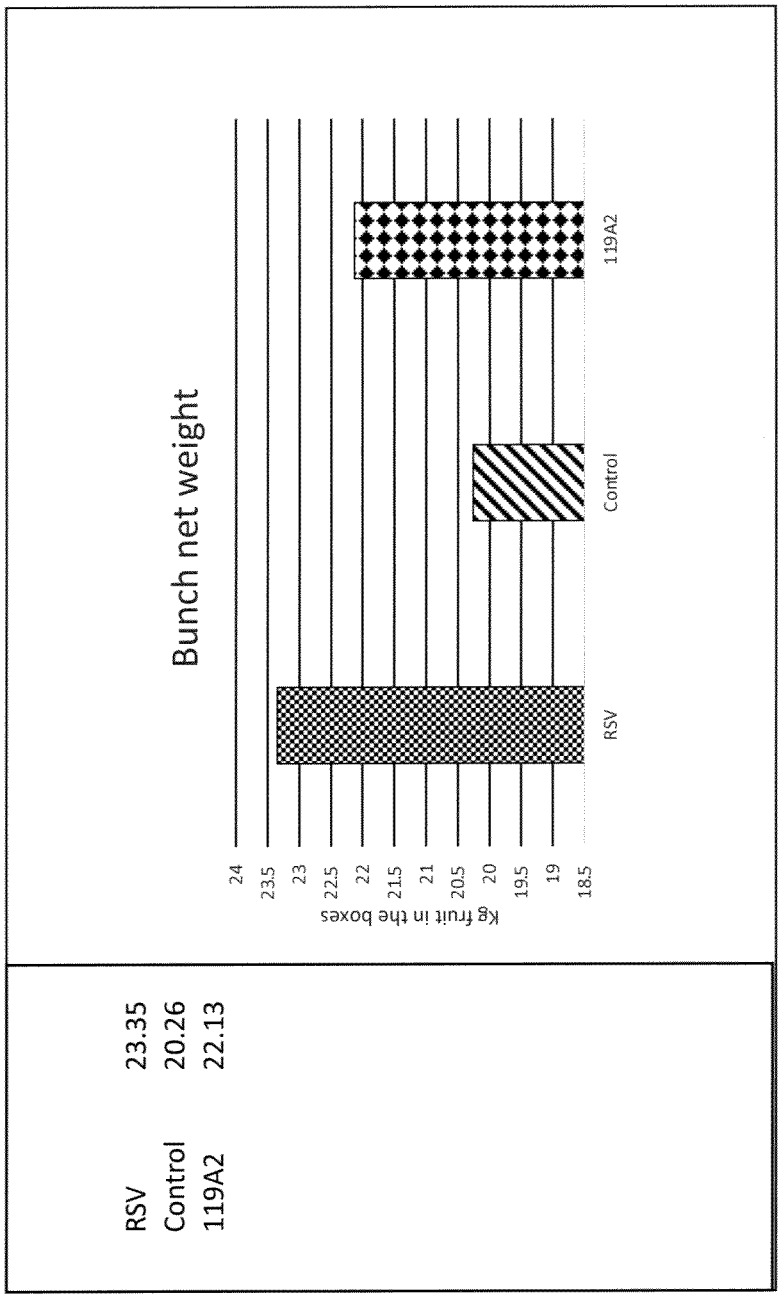
| | |
|---|---|
| RSV | 23.35 |
| Control | 20.26 |
| 119A2 | 22.13 |
Figure 2: Bunch Weight

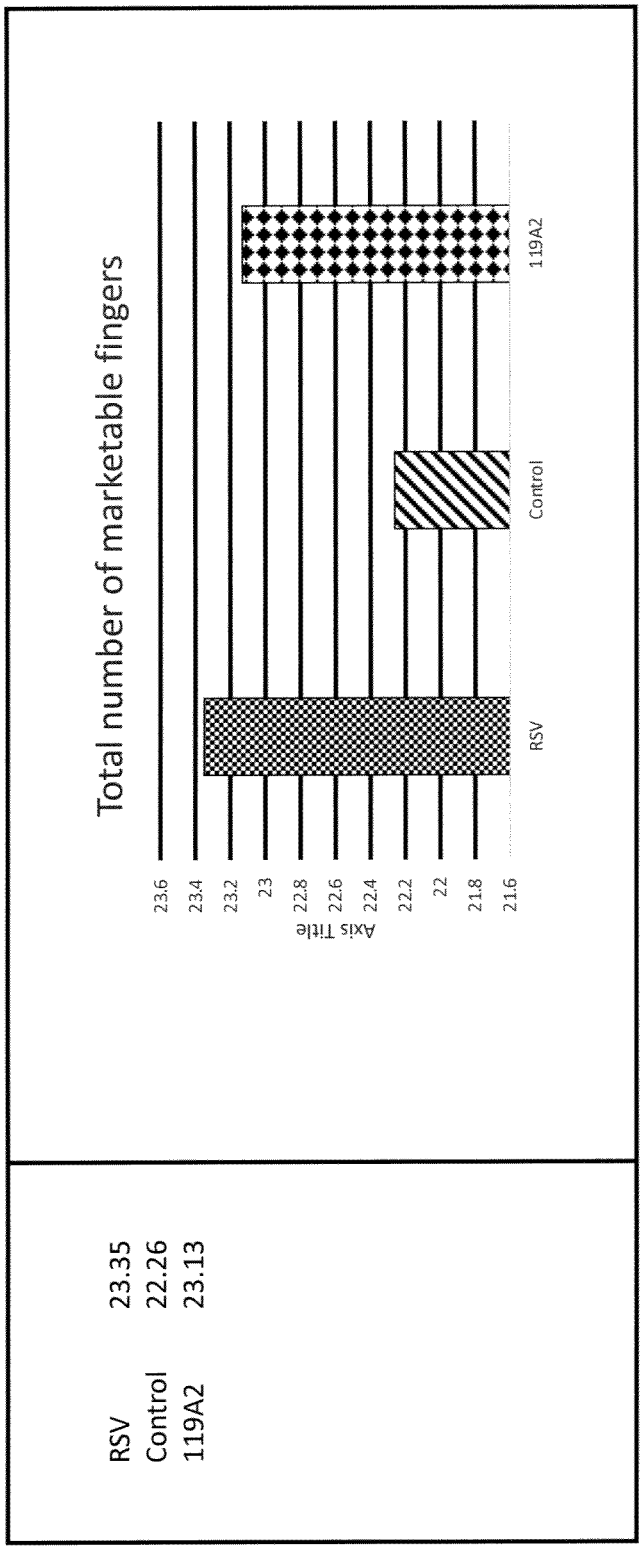
Figure 3: Number of Marketable Fingers
| | |
|---|---|
| RSV | 23.35 |
| Control | 22.26 |
| 119A2 | 23.13 |

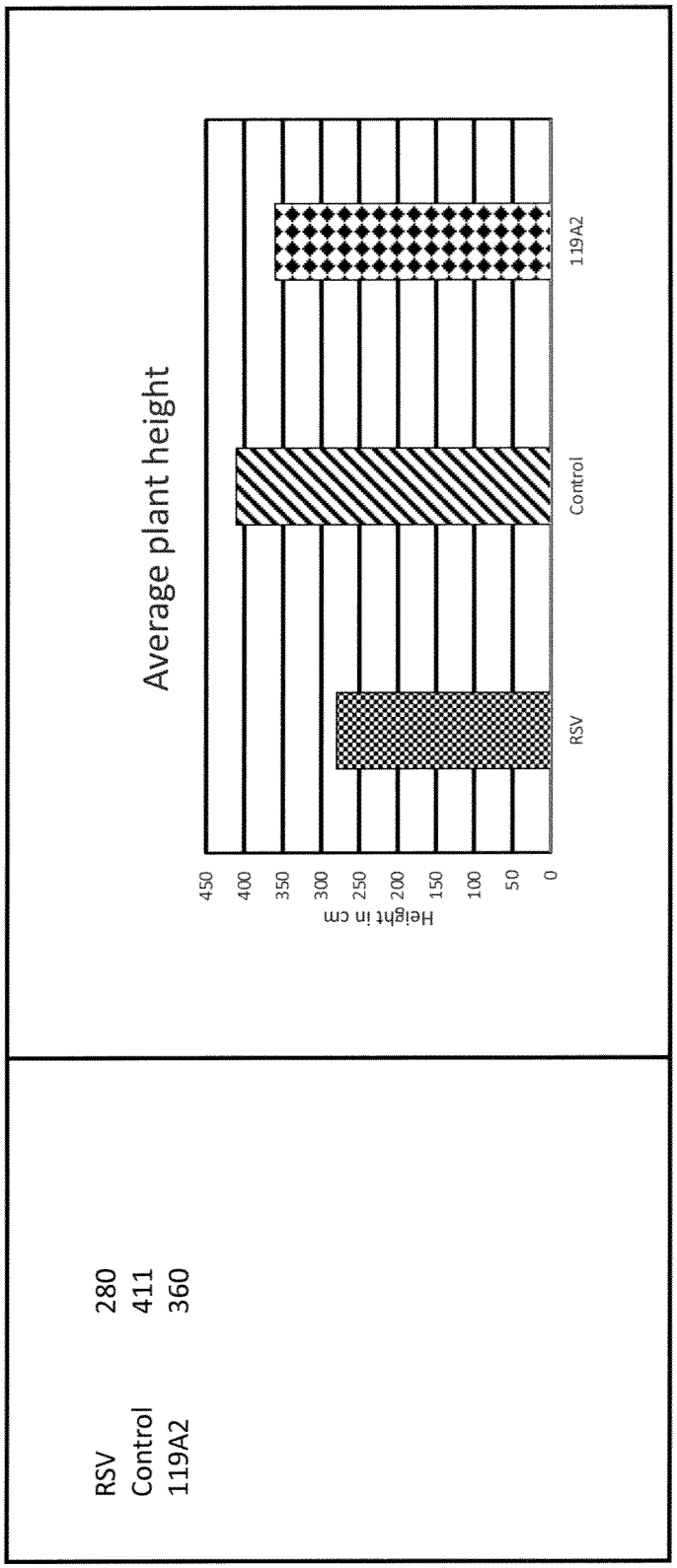
| | |
|---|---|
| RSV | 280 |
| Control | 411 |
| 119A2 | 360 |
Figure 4: Average Plant Height

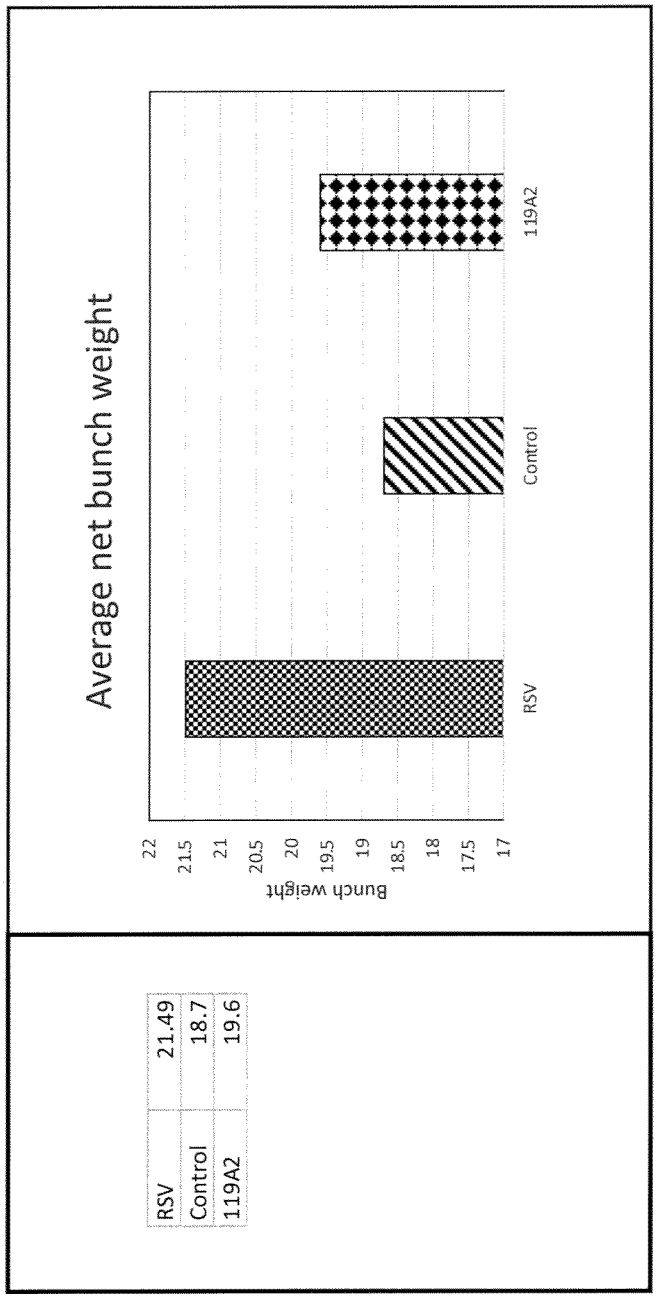
| | |
|---|---|
| RSV | 21.49 |
| Control | 18.7 |
| 119A2 | 19.6 |
Figure 5: Average Net Bunch Weight

Figure 6: Average Number of Marketable Fingers
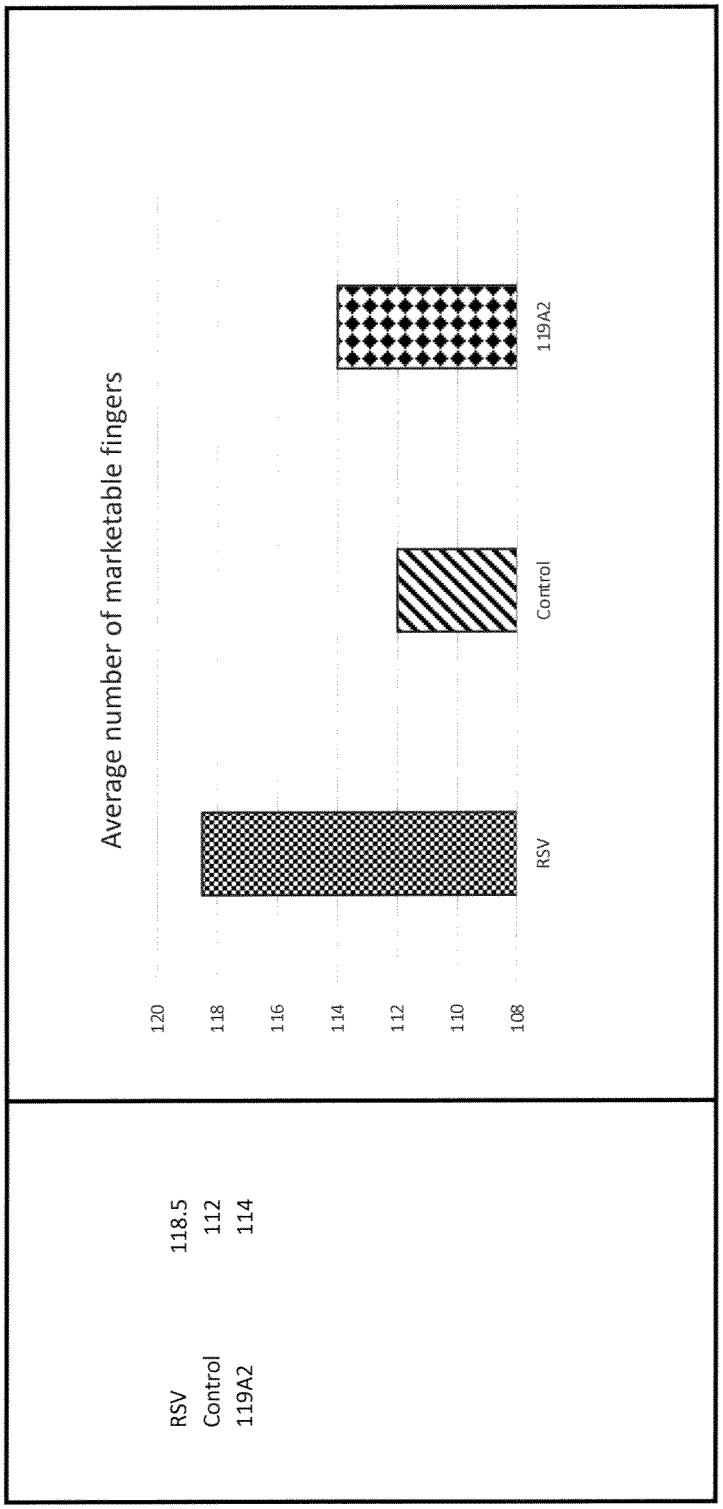
| | |
|---|---|
| RSV | 118.5 |
| Control | 112 |
| 119A2 | 114 |

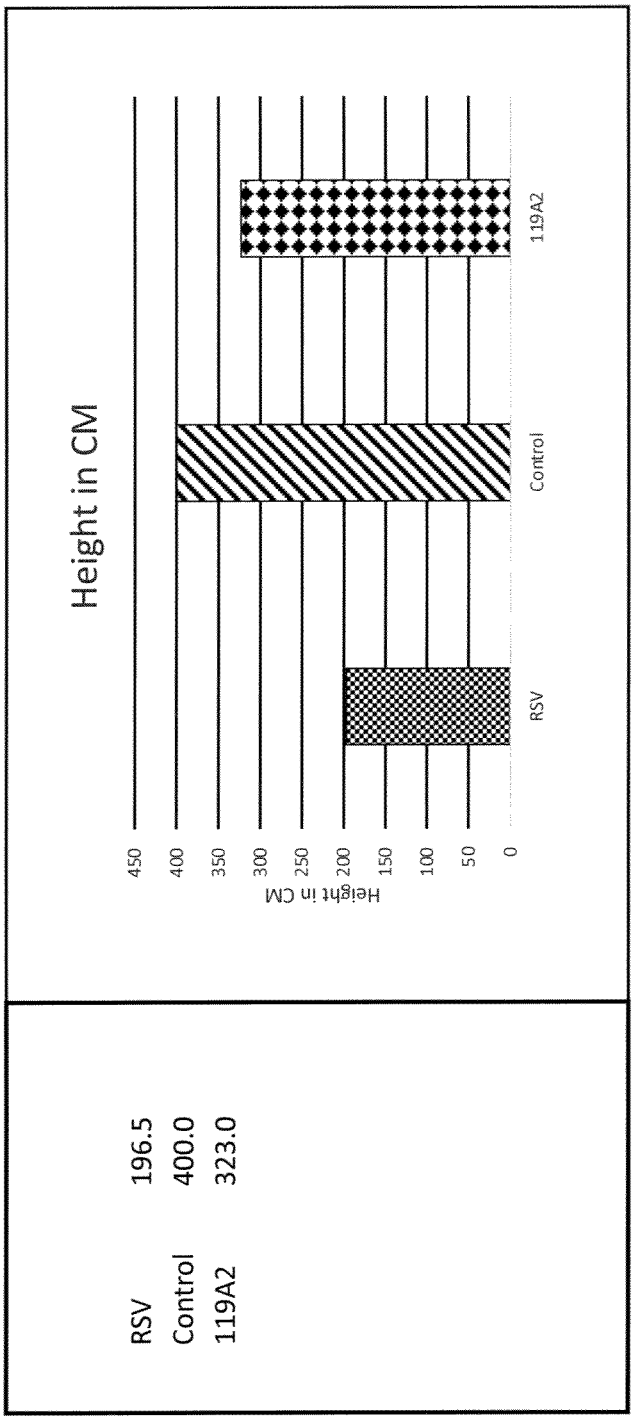
Figure 7: Height in CM
| | |
|---|---|
| RSV | 196.5 |
| Control | 400.0 |
| 119A2 | 323.0 |

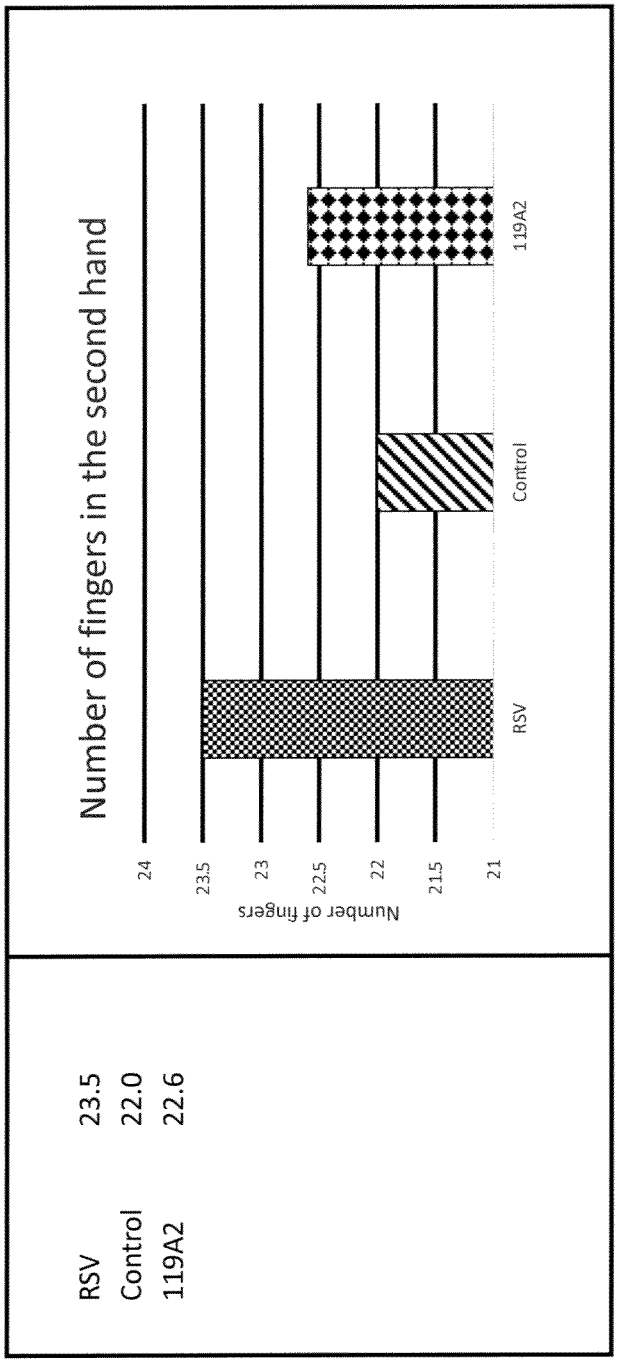
| | |
|---|---|
| RSV | 23.5 |
| Control | 22.0 |
| 119A2 | 22.6 |
Figure 8: Number of Fingers in the second hand

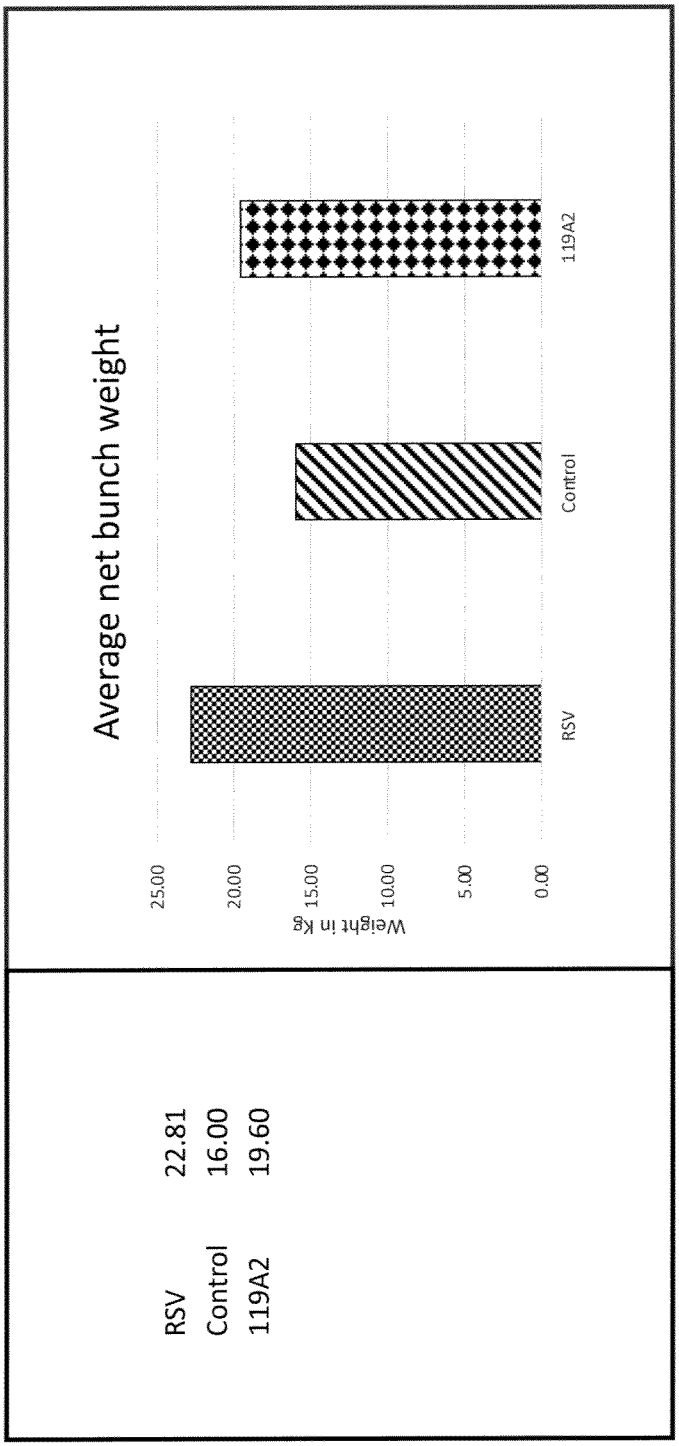
| | |
|---|---|
| RSV | 22.81 |
| Control | 16.00 |
| 119A2 | 19.60 |
Figure 9: Average Net Bunch Weight

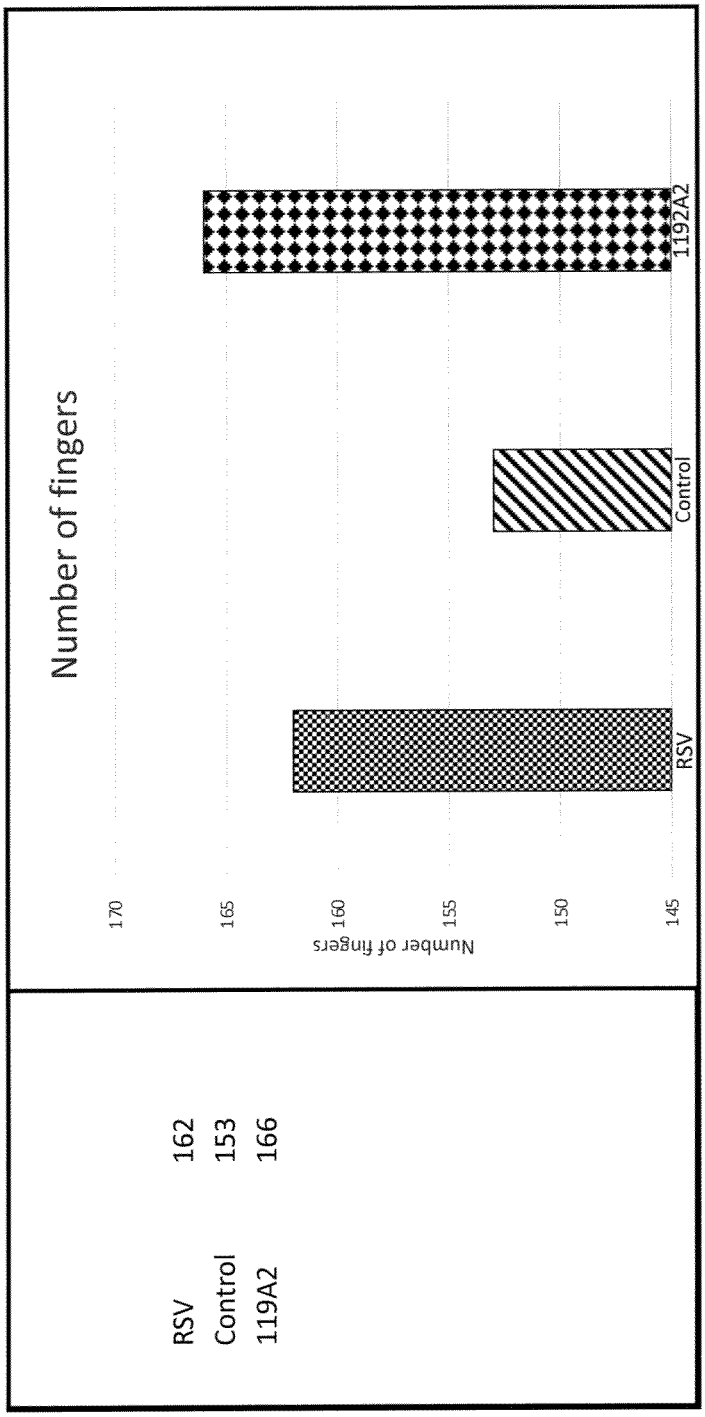
| | |
|---|---|
| RSV | 162 |
| Control | 153 |
| 119A2 | 166 |
Figure 10: Number of Fingers

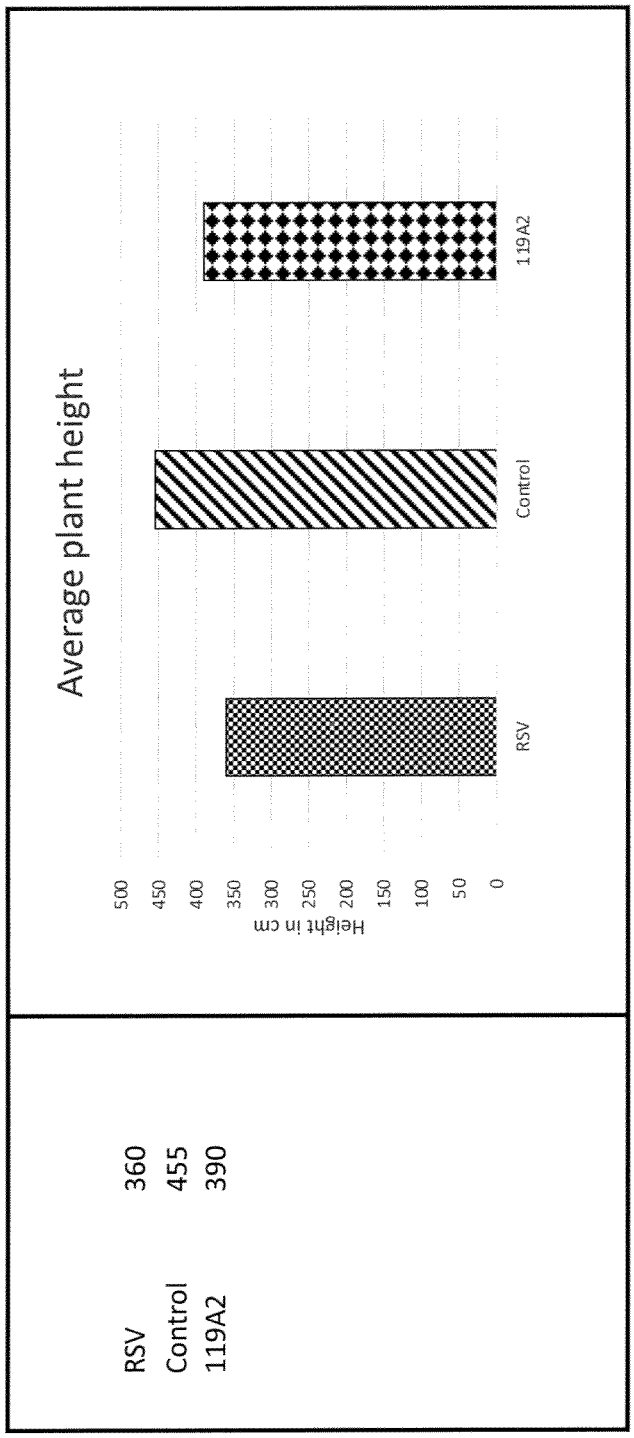
| | |
|---|---|
| RSV | 360 |
| Control | 455 |
| 119A2 | 390 |
Figure 11: Average Plant Height

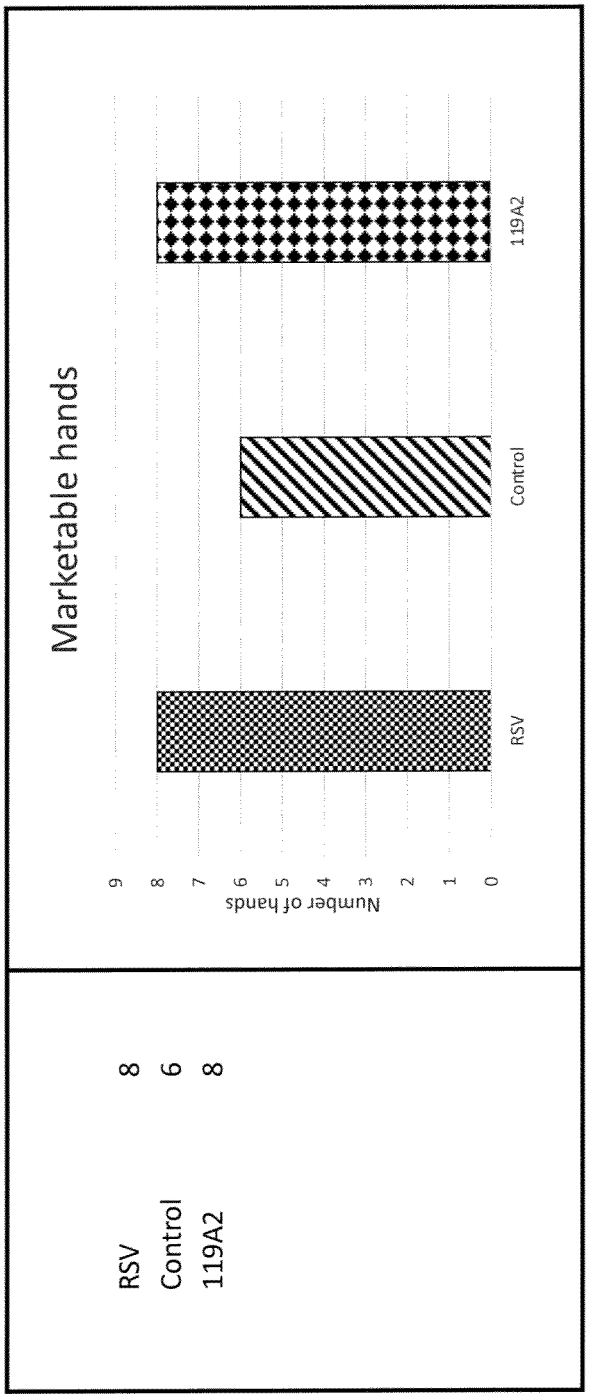
| | |
|---|---|
| RSV | 8 |
| Control | 6 |
| 119A2 | 8 |
Figure 12: Marketable Hands

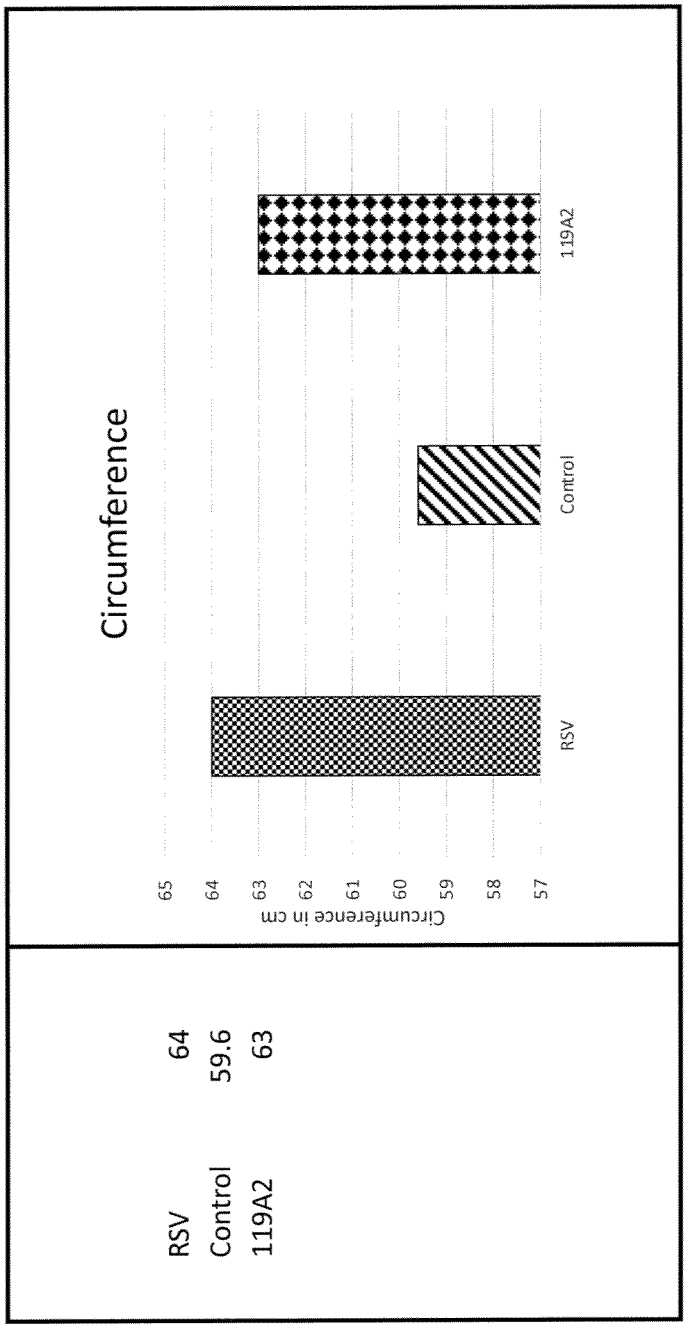
| | |
|---|---|
| RSV | 64 |
| Control | 59.6 |
| 119A2 | 63 |
Figure 13: Circumference

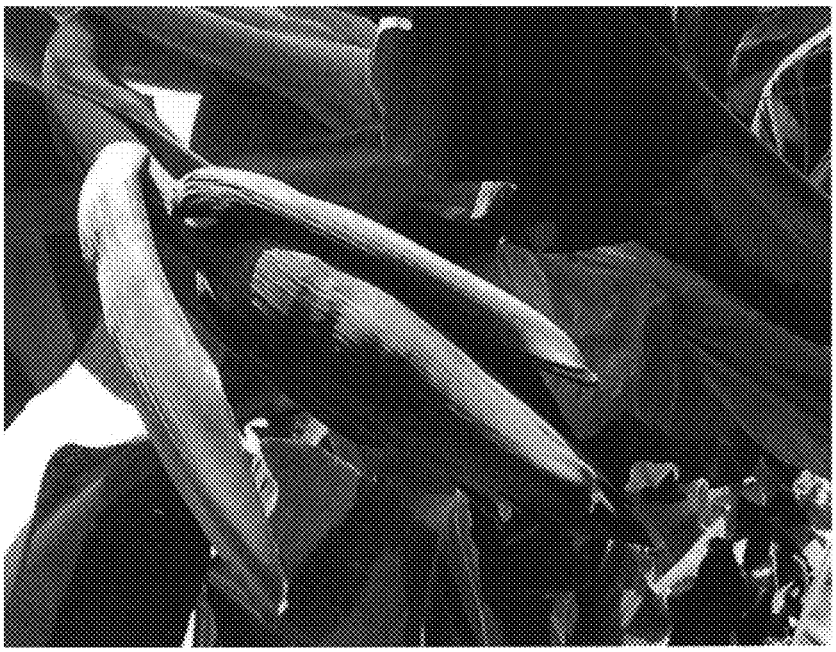
Figure 14 – RSV inflorescence

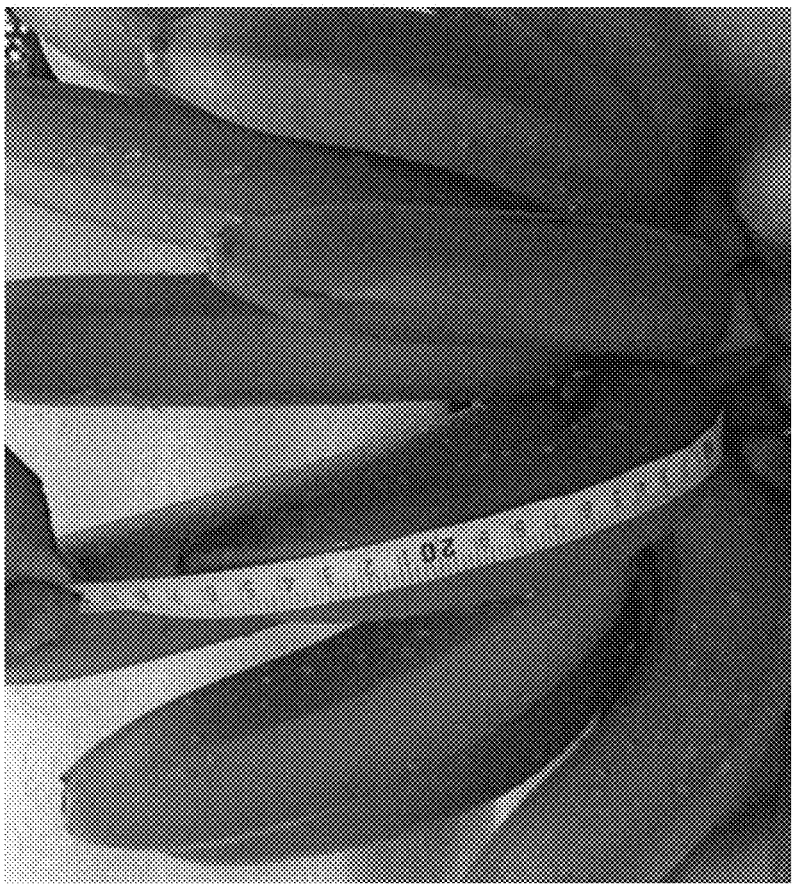
Figure 15 – fruit in hand 2 from the top of the bunch